United States Patent
Isele et al.

(10) Patent No.: US 10,667,963 B2
(45) Date of Patent: *Jun. 2, 2020

(54) NONWOVEN THERMAL BONDING PATTERN WITH LOW FUZZ

(71) Applicant: The Procter & Gamble Company, Cincinnati, OH (US)

(72) Inventors: Olaf Erik Alexander Isele, West Chester, OH (US); Donald Raymond Kearney, Springdale, OH (US); Nicole Anja Reichardt, Sulzbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 622 days.

This patent is subject to a terminal disclaimer.

(21) Appl. No.: 15/356,705

(22) Filed: Nov. 21, 2016

(65) Prior Publication Data

US 2017/0151101 A1 Jun. 1, 2017

Related U.S. Application Data

(60) Provisional application No. 62/260,731, filed on Nov. 30, 2015.

(51) Int. Cl.
*A61F 13/515* (2006.01)
*D04H 5/06* (2006.01)
(Continued)

(52) U.S. Cl.
CPC ...... *A61F 13/515* (2013.01); *A61F 13/15203* (2013.01); *A61F 13/513* (2013.01);
(Continued)

(58) Field of Classification Search
CPC ... D04H 3/14; D04H 1/54; D04H 5/06; A61F 13/51476
See application file for complete search history.

(56) References Cited

U.S. PATENT DOCUMENTS 3,616,157 A * 10/1971 Smith .................... A47L 13/16
428/171
3,692,622 A 9/1972 Dunning
(Continued)

FOREIGN PATENT DOCUMENTS

| WO | WO 00/04215 | 1/2000 |
| WO | WO 01/12427 | 2/2001 |
| WO | WO 2014/078247 | 5/2014 |

(Continued)

OTHER PUBLICATIONS

International Search Report and Written Opinion, PCT/US2016/060218, dated Jan. 26, 2017.
All Office Actions, U.S. Appl. No. 15/356,711.

*Primary Examiner* — Elizabeth C Imani
(74) *Attorney, Agent, or Firm* — Christian M. Best (57) ABSTRACT

A nonwoven extending in a machine direction and a perpendicular cross-machine direction and having fibers bonded by a pattern of thermal bonds. The thermal bonds comprise larger bonds having an individual area of at least 1.0 mm$^2$, in particular at least 1.5 mm$^2$; and smaller bonds having an individual area of less than 1.0 mm$^2$, in particular from about 0.10 mm$^2$ to about 1.0 mm$^2$. There are at least as many smaller bonds as larger bonds, the ratio of the number of smaller bonds may be in particular about two.

18 Claims, 3 Drawing Sheets

(51) Int. Cl.
*D04H 1/544* (2012.01)
*D04H 1/4291* (2012.01)
*D04H 3/14* (2012.01)
*D04H 1/54* (2012.01)
*D04H 1/74* (2006.01)
*A61F 13/514* (2006.01)
*A61F 13/511* (2006.01)
*A61F 13/15* (2006.01)
*A61F 13/513* (2006.01)

(52) U.S. Cl.
CPC .. *A61F 13/51104* (2013.01); *A61F 13/51121* (2013.01); *A61F 13/51401* (2013.01); *A61F 13/51476* (2013.01); *A61F 13/51496* (2013.01); *D04H 1/4291* (2013.01); *D04H 1/54* (2013.01); *D04H 1/544* (2013.01); *D04H 1/74* (2013.01); *D04H 3/14* (2013.01); *D04H 5/06* (2013.01); *A61F 2013/15406* (2013.01); *A61F 2013/51377* (2013.01)

(56) References Cited

U.S. PATENT DOCUMENTS

| | | | |
|---|---|---|---|
| 5,620,779 | A | 4/1997 | Levy et al. |
| 6,286,145 | B1 | 9/2001 | Welchel et al. |
| 6,383,958 | B1 | 5/2002 | Swanson et al. |
| 6,468,931 | B1 | 10/2002 | Reeder et al. |
| 6,620,490 | B1 * | 9/2003 | Malchow ............ B32B 7/04 428/196 |
| 8,530,722 | B2 | 9/2013 | Rinnert et al. |
| 2004/0241399 | A1 | 12/2004 | Marmon et al. |
| 2008/0032579 | A1 | 2/2008 | Abed et al. |
| 2012/0156447 | A1 | 6/2012 | Hein et al. |
| 2013/0253461 | A1 * | 9/2013 | Xu .................. A61F 13/511 604/384 |
| 2014/0072767 | A1 | 3/2014 | Klaska et al. |
| 2018/0025747 | A1 | 11/2018 | Bremer et al. |

FOREIGN PATENT DOCUMENTS

WO  WO 2014/200794   12/2014
WO  WO 2015/095514   6/2015

* cited by examiner

NONWOVEN THERMAL BONDING PATTERN WITH LOW FUZZ

CROSS REFERENCE TO RELATED APPLICATION

This application claims the benefit, under 35 U.S.C. § 119(e), to U.S. Provisional Patent Application Ser. No. 62/260,731, filed on Nov. 30, 2015, which is herein incorporated by reference in its entirety.

FIELD OF THE INVENTION

The invention is directed to an improved thermal bonding pattern for the fibers of a nonwoven. The nonwoven may be used in particular as a topsheet or in a backsheet in absorbent articles such as taped diapers, diaper pants or feminine pads.

BACKGROUND OF THE INVENTION

Absorbent articles for personal hygiene of the type indicated above are designed to absorb and contain body exudates, in particular large quantity of urine. These absorbent articles comprise several layers, typically a topsheet on the wearer-facing side, a backsheet on the garment-facing side and in-between an absorbent core, among other layers. An acquisition and/or a distribution layer may be further provided between the absorbent core and the topsheet. Topsheets are usually either made of a nonwoven or a formed film. Backsheets are typically made of a fluid-impermeable plastic film sometimes doubled on its external side by a nonwoven layer to provide a better feel. It is known to consolidate nonwovens by applying a thermal bonding pattern to the fibers. A commonly used technique involves passing the web of fibers between two calender rolls. One of the roll is typically smooth, and the other roll comprises protrusions having the shape and the disposition of the desired thermal bonding pattern. Typically the calender roll with the protrusion may be heated so that enough heat is applied to the web to locally melt the fibers of the web according to the desired thermal bonding pattern. This and other techniques to provide a bonding pattern on a nonwoven are disclosed in details for example in WO00/04215 (assigned to Fibervisions Inc.).

Various thermal bonding patterns have been suggested. WO01/12427A1 (assigned to First Quality Fibers, Inc) for example discloses a nonwoven with a non-symmetrical bonding configuration. The bonds have a generally oval shape and are oriented in different directions. US2014/0072767 (assigned to Pegas Nonwovens S.R.O.) discloses various bonding patterns including convex "wing" shapes and sigmoid "S" shapes. U.S. Pat. No. 8,530,722 (Rinnert et al.) discloses a colored topsheet having a basis weight of from 12 to 18 gsm and comprises a plurality of bonded points. Each of the bonded points has a surface area of from 2 mm$^2$ to 5 mm$^2$ and the cumulated surface area of the plurality of bonded points is from 10 to 25% of the total surface area of the top sheet. The bond points exemplified are generally round and have all the same shape.

The present inventors have found that many of the patterns of the prior art exhibit a relatively large amount of broken fibers that stick out of the surface of the nonwoven, referred to as fuzz. These broken fibers are generally undesirable as they reduce the quality perception of the nonwoven. The invention provides an efficient bonding pattern for the fibers of the nonwoven resulting in smaller broken fibers sticking out of the plane of the nonwoven ("fuzz") while keeping desirable attributes such as softness, flexibility, integrity, absorbency and cost-effectiveness.

SUMMARY OF THE INVENTION

The invention is directed to a nonwoven extending in a machine direction (MD) and a perpendicular cross-machine direction (CD), the nonwoven comprising fibers bonded by thermal bonds. In a first aspect, the thermal bonds comprise:

larger bonds having an individual area of at least 1.0 mm$^2$, in particular at least 1.5 mm$^2$; and smaller bonds having an individual area of less than 1.0 mm$^2$, in particular from 0.10 mm$^2$ to 1.0 mm$^2$.

There is at least as many smaller bonds as larger bonds, and there may be advantageously more smaller bonds than larger bonds. The ratio of the number of smaller bonds to the number of larger bonds may be at least 1.2, or at least 1.5, or even 2.0 or more. The number of the different bonds are of course counted on an area of the nonwoven representative of the whole of the bonding pattern.

The inventors have found that by combining larger bonds with smaller bonds, the objects of the invention can be achieved. Although not wishing to be bound by theory, the inventors believe that the fibers in a nonwoven although seemingly randomly aligned still have a tendency to align in machine direction (MD), i.e. the direction of the production of the web. The inventors believe that if these generally MD-aligned fibers are not sufficiently bonded, in particular if too many MD-oriented bond-free "channels" are present, breakage of the fibers in these channels can disproportionally increase the fuzz on the nonwoven. The inventors believe that breakage may be in particular caused by the abrasion of the nonwoven during wear against the skin or the clothes of the wearer. The abrasion may be principally suffered in the front-to-back direction of the nonwoven i.e. typically the machine direction (MD) of the nonwoven.

The present invention combines larger bonds with smaller bonds. The larger bonds provide a good integrity to the web by bonding a large amount of fiber, however it was found that having only larger bonds may not be desirable as the overall softness of the nonwoven may be decreased. The smaller bonds between the larger bonds help disrupting any bond-free "channels" between the larger bonds. It was found that having smaller thermal bonds in addition to fewer larger bonds did not provide a noticeable softness disadvantage due to their small individual areas.

This and other aspects of the invention is further described and illustrated in the following description and accompanying drawings.

DETAILED DESCRIPTION OF THE INVENTION

Introduction

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Nonwovens

The nonwovens comprising the thermal bonds of the invention may be according to any types of nonwovens known in the art. The term nonwoven typically refers to a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to more than 0.2 mm and they come in several different forms such as short fibers (known as staple, or chopped), continuous single fibers (filaments or monofilaments), untwisted bundles of continuous filaments (tow), and twisted bundles of continuous filaments (yam).

Nonwoven webs can be formed by many processes such as meltblowing, spunbonding, solvent spinning, electrospinning, carding and airlaying. Nonwovens are typically continuously made by depositing and entangling the fibers on a moving web support. The direction of production of the web is the machine direction (MD), and the direction perpendicular is referred to as the cross-machine direction (CD). The machine direction is the direction along which the web is continuously formed, for example by a spunbonding process, as is known in the art. The machine direction is the continuous or "long" direction of the web, along which the web may be rolled in a roll before being converted in an absorbent article's converting line. The machine direction of the web is thus typically the same direction as the longitudinal direction of the finished article in which the nonwoven is incorporated. The thermal bonding pattern is typically applied to the nonwoven web immediately after the nonwoven web has been formed. The properties of the webs such as strength and stretchability may typically be different when measured in MD or CD. The thermal bond pattern may be typically directly applied after the deposition of the fibers, in particular but not limited to, by passing the nonwoven between two calender rolls.

The basis weight of nonwoven webs is usually expressed in grams per square meter ($g/m^2$ or gsm). The nonwovens of the invention may have any usual basis weight, for example the basis weight may range from 10 gsm to 30 gsm, in particular form 12 gsm to 20 gsm. This range may be particularly useful for a topsheet in an absorbent article, as it provide a good compromise between functionality and economy of material. The basis weight may of course be lower than 10 gsm or higher than 30 gsm for other applications or if other considerations are present. The nonwoven may also be used in other layers of an absorbent article, for example the outer cover of the backsheet. An absorbent article typically comprises a topsheet on its wearer-facing side, a backsheet on its garment-facing side and an absorbent core between the topsheet and the backsheet, and optionally an acquisition layer between the topsheet and the core, as well as longitudinally extending barrier leg cuffs which may be elasticized to prevent side leakage. Any of these layers may comprise a nonwoven according to the invention. Exemplary disclosure of absorbent articles are for example included in WO2014/200794 A1 (Bianchi et al.), WO2015/095514 (Laveeta).

In a further aspect, the nonwoven may be colored, e.g. by introducing a pigment in the fibers comprising the nonwoven and/or the nonwoven may have an opacity index of from 15% to 50% as measured by the test described herein. The nonwoven may in particular be used as a topsheet above another layer such as an acquisition layer comprising a visual signal, for example as disclosed in WO2014/078247 A1 (Rosati, et al). It was found that the larger thermal bonds may be more relatively transparent and improve the visibility of the visual signal. This was found to be especially the case when the topsheet was made of multilobal fibers, in particular trilobal fibers, as exemplarily disclosed in US2008/0032579 A1 (Abed at al.).

General Description of the Pattern Formed by the Thermal Bonds

The thermal bonds of the invention comprise larger bonds and smaller bonds having different individual areas. The larger thermal bonds may, on one side, all have the same size and shape, and the smaller bonds may, on the other side, also all have the same size and shape, as will be discussed further below with reference to the examples of the Figures. All bonds having the same size may all have the same orientation, but advantageously bonds having the same size may also have different orientations, in particular there may be two types of larger bonds having two different orientations and/or there may be two types of smaller bonds having two different orientations. It is however not excluded that more complex bonding patterns may be used, in particular wherein the pattern comprises more than two sizes of bonds.

According to the invention, the larger bonds are defined herein as bonds having an individual area of at least 1.0 $mm^2$. The larger bonds may be more restrictively defined as thermal bonds having an individual area of at least 1.5 $mm^2$ or more than 2.0 $mm^2$. There is no maximum size for the larger bonds, but in general the bonds may have an individual area of less than 10 $mm^2$. As indicated above, the larger bonds provide the web with an improved integrity by bonding a large amount of fibers. The larger bonds are typically visually recognizable at the surface of the nonwoven. For example the user of an absorbent article having a topsheet according to the invention may typically recognize the presence of the larger bonds. The bonding pattern further comprises smaller bonds, defined has having an individual area of less than 1.0 $mm^2$, in particular from 0.10 $mm^2$ to less than 1.0 $mm^2$. It was found that the smaller bonds help disrupting the channel-like bond-free areas between the larger bonds. It is believed that the smaller bonds can thus considerably reduce the occurrence of long broken fibers from sticking out of the surface of the nonwoven (fuzz). Whereas having only larger bonds may not be desirable as the overall softness of the nonwoven may be decreased if too many larger bonds are present, it was found however that having smaller thermal bonds in addition to fewer larger bonds did not provide a noticeable softness disadvantage.

Figure 3:
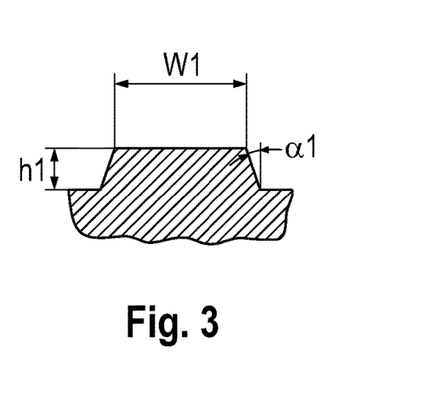
FIG. 3 is a schematic cross-section of the protrusion of a calender roll for the larger bonds at a scale 10:1.
Figure 4:
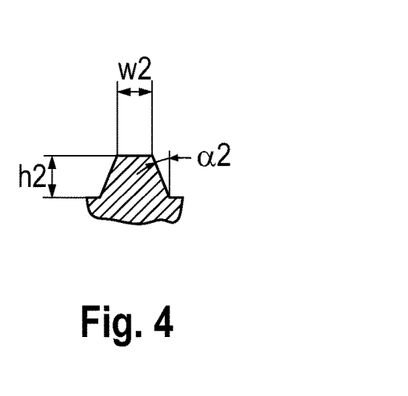
FIG. 4 is a schematic cross-section of the protrusion of a calender roll for the smaller bonds at a scale 10:1.
Figure 5:
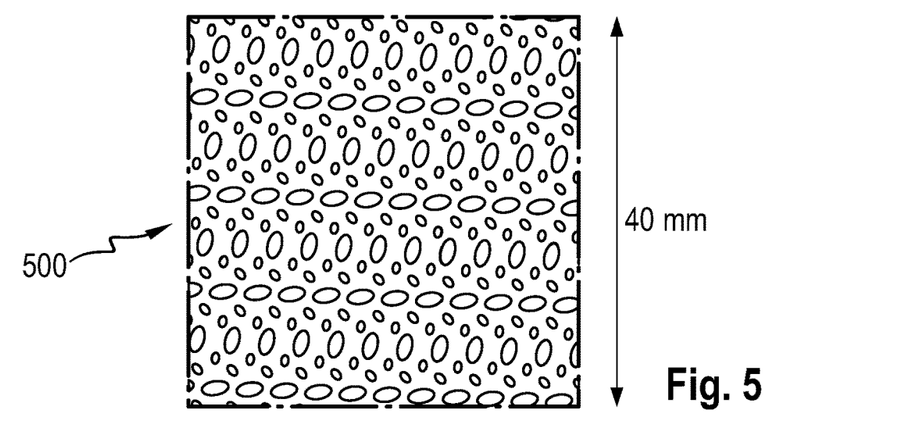
FIGS. 5-10 show different alternative exemplary bonding patterns.
Figure 6:
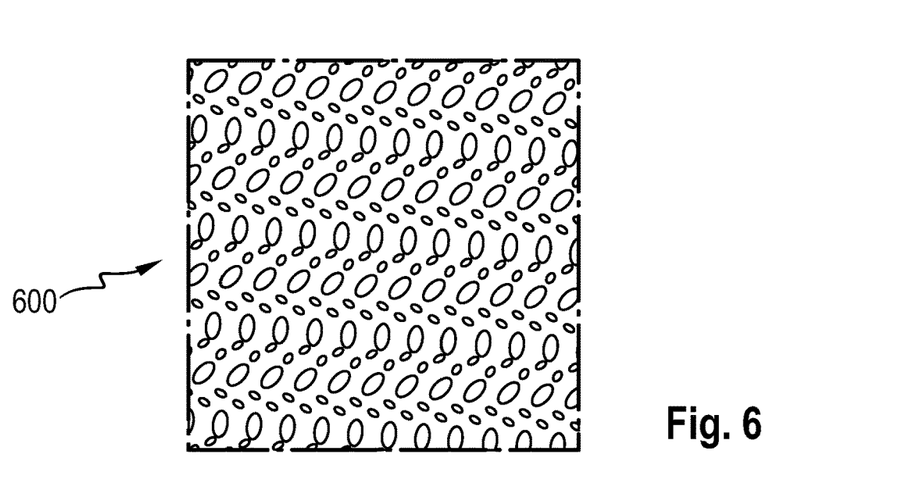
Figure 7:
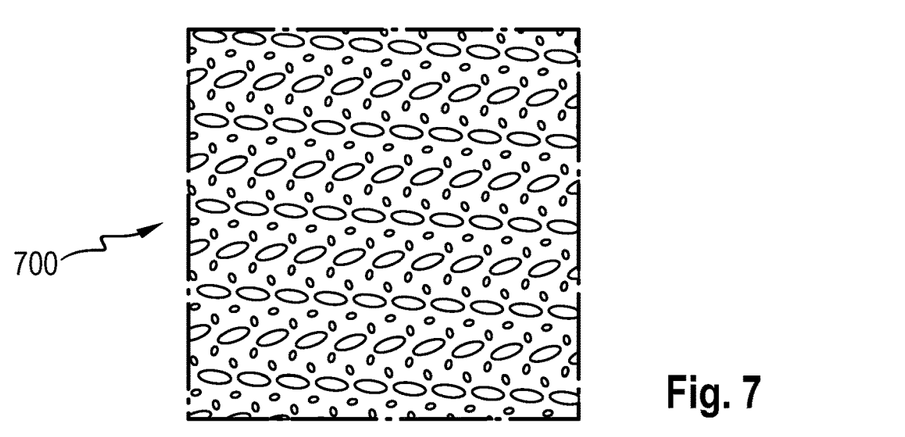
Figure 8:
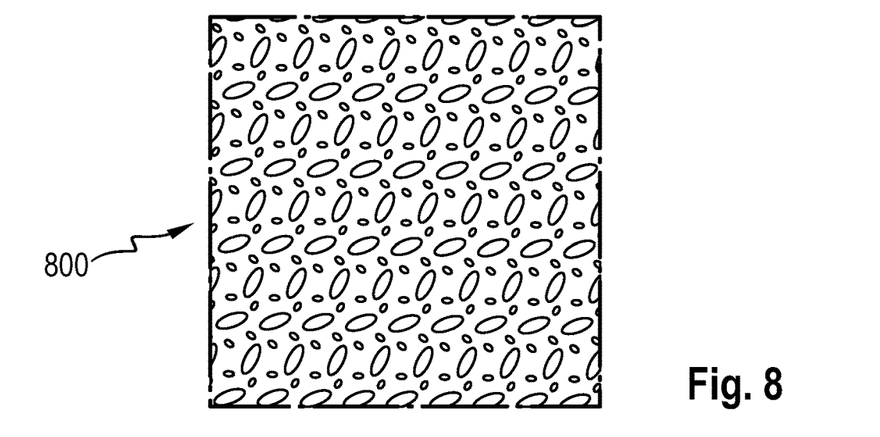
Figure 9:
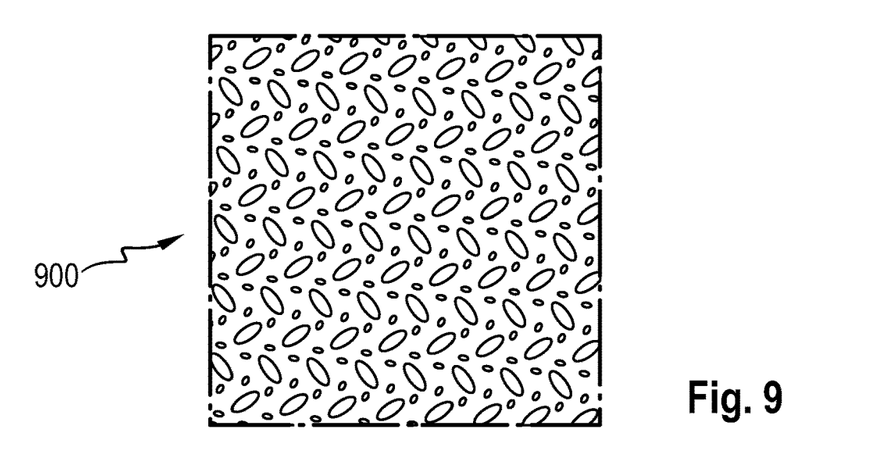
Figure 10:
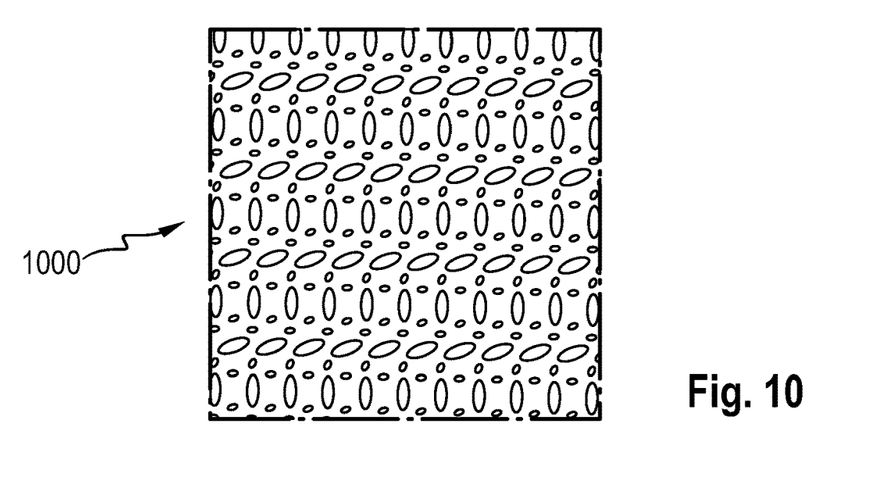

The thermal bonds pattern, including shape, size and orientation of the bonds, is typically determined by the tool used to form the bonds on the nonwoven. As indicated previously, thermal bonds are typically provided on a nonwoven by passing the web of fibers directly after its formation between two calender rolls. Typically, one of the calender rolls will comprise protrusions corresponding to the desired bonding pattern. FIGS. 3 and 4 for example show cross-sections of two protrusions on the calender rolls. The size and shape of the individual bonding points corresponds to the size and shape of the flat, plateau-shaped upper surface of the protrusions. The individual sizes of the thermal bonds can be most easily determined by considering the technical drawings for the calender tool (or other tool used to emboss the thermal bonds, the present invention not being limited to thermal bonds obtained by calender rolls). Typically, technical drawings indicating the dimensions including the individual surface areas of the different thermal bonds will be generated by or for the tool manufacturer to engrave the desired pattern on the calender roll. Alternatively, it is also possible to measure the dimensions of the protrusions of the calender roll, or any other tools used to make the thermal bonds. Finally, if the technical drawings and the bonding tool are not directly available, the size, shape and orientation of the individual bonds may be directly measured on the nonwoven as an end product, for example using microscopic pictures and standard image analysis software.

The bonding pattern comprises at least as many smaller bonds as larger bonds. The ratio of the count of smaller bonds to the count of the larger bonds on a representative area may be in particular at least 1.2 (i.e. there are 20% more smaller bonds than larger bonds on a count basis), in particular the count ratio may be at least 1.5, more particularly 2.0 (i.e. 100% or more smaller bonds than larger bonds) or more. In the examples shown in the Figures discussed further below, there are twice as many smaller bonds than larger bonds (so a ratio of 2:1). However because the individual sizes of the smaller bonds is much smaller than the larger bonds, the larger bonds still typically provide the largest overall bonding area on the nonwoven.

The proportion of the smaller bonds relative to the larger bonds can be simply assessed by selecting a representative surface of the nonwoven and counting how many of each of the bonds are present. This may be expressed in numbers of bonds per unit of surface, per square centimeter for example. Since the ratio of the number of the smaller bonds to the larger bonds is then calculated, the unit of surface is not critical. The information may also be more simply directly read from the technical drawings used to make the tool such as the calendar roll if these are available.

The thermal bonds of the invention may further advantageously comprise any of the following features alone or in combination. The larger and the smaller bonds may be generally rounded without sharp angle as in a circle or an oval. The larger and smaller bonds may be elongated, with a major dimension (i.e. length) measured along a major direction and a minor dimension (i.e. width) measured along a minor direction perpendicular to the major direction. The major dimension (L1) of the larger bonds may be in particular at least 50% higher than the major dimension (l1) of the smaller bonds. The major dimension of the larger bonds may in particular be at least 1.50 mm, or at least 1.75 mm, or at least 2.00 mm, and the major dimension of the smaller bond may be less than 1.50 mm, in particular less than 1.25 mm, or less than 1.00 mm. The minor dimension of the larger bonds (W1) may for example range from 0.9 mm to 3.6 mm and the minor dimension (w2) of the smaller bonds may for example range from 0.26 mm to 1.0 mm.

At least some of the larger elongated thermal bonds may have a ratio of the major dimension to the minor dimension ranging from 1.05 to 2.0, and at least some of the smaller elongated thermal bonds have a ratio of the major dimension to the minor dimension ranging from 1.10 to 2.5.

The larger bonds and/or the smaller bonds may have their major direction oriented at an angle of at least 10° relative to the machine direction (MD) of the nonwoven, and preferably more than 10° for example from 15° to 90°. This provides for an increased reduction of the width of MD-oriented bond-free channels between the thermal bonds as discussed above. It is further possible that less than 20% of the total number of the thermal bonds, in particular less than 10% of all the thermal bonds are oriented parallel to the machine direction. There may also be no thermal bonds oriented in the machine direction. All angles are reported herein in absolute value (it is irrelevant whether they are measured clockwise or anti-clockwise). Similarly, all the patterns discussed herein can be duplicated as a reflection across the MD axis or a reflection across the CD axis and these reflections are expected to give the same fuzz reducing result.

The larger bonds may comprise differently oriented larger bonds, in particular wherein the angle formed by the major dimensions of the differently oriented larger bonds is at least 20°. The smaller bonds may also comprise differently oriented smaller bonds, in particular wherein the angle formed by the larger dimensions of the differently oriented smaller bonds is at least 20°.

At least some of the larger bonds and/or the smaller bonds, and preferably all of the thermal bonds, may be disposed in rows generally aligned with the cross-machine direction (CD) or machine-direction (MD). By "generally aligned" with the CD or MD, it is meant that the rows may optionally and advantageously have a pitch angle (P) ranging from 0 to 15 degrees relative to the CD or MD direction, in particular from 0.5 to 10 degrees, or from 1 to 5 degrees. Having such a pitch angle ensure that the bonds in two identical repeating rows are not perfectly aligned with the machine direction. Additionally, it is advantageous that the bonds in two adjacent rows are not aligned in machine direction, but rather that the bonds in consecutive rows are staggered so that the bonds are maximally disrupting or "breaking" the MD oriented bond-free "channels" between the bonds. As indicated before, the pitch angle is reported in absolute value, as it makes no difference whether a positive or negative rotation is chosen for the pattern pitch angle.

The distance between two repeating rows having the same type of larger bonds (repeat in height D2) may for example range from 4.0 mm to 16 mm. The distance between two adjacent rows of the larger bonds of different orientation (repeat in height D2/2) may for example range from 2.0 mm to 8 mm. The smaller bonds may be disposed between the rows of larger bonds. The distance center-to-center of two adjacent bonds in a given row (repeat in width D1) may for example range for at least some of the bonds from 2 mm to 8 mm, in particular from 3 mm to 7 mm. There may be for example two rows of smaller bonds between two rows of larger bonds. In general, all the bonds in a row may be of the same type as defined by size, shape and orientation, but it is not excluded that in some or all the rows bonds of different types may be present.

The bonding area of all the thermal bonds of the pattern may advantageously represent from 17% to 30% of the area of the nonwoven on which the pattern is applied, in particular from 19% to 28%, more particularly from 21% to 26% of the area of the nonwoven. These ranges were found to provide the optimum anti-fuzz benefits while retaining the softness attribute of the nonwoven. The average amount of thermal bonds (all included) per unit of surface may in particular range from 5 per cm$^2$ to 58 per cm$^2$, in particular from 10 per cm$^2$ to 30 per cm$^2$, but other values are not excluded.

The invention will now be further illustrated with reference to the examples as described in the Figures. For ease of discussion, the nonwoven and the thermal bonds may be discussed with reference to the numerals referred to in these Figures. However it should be understood that these exemplary embodiments and the numerals are not intended to limit the scope of the claims, unless specifically indicated. Nothing in this description should be considered limiting the scope of the claims unless explicitly indicated otherwise.

EXAMPLES

Figure 1:
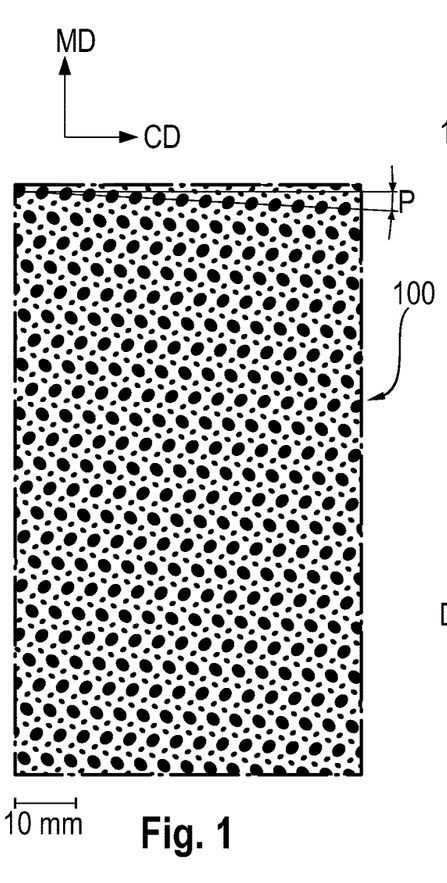
FIG. 1 shows of an exemplary thermal bonding pattern at a scale 1:1 according to the invention.
Figure 2:
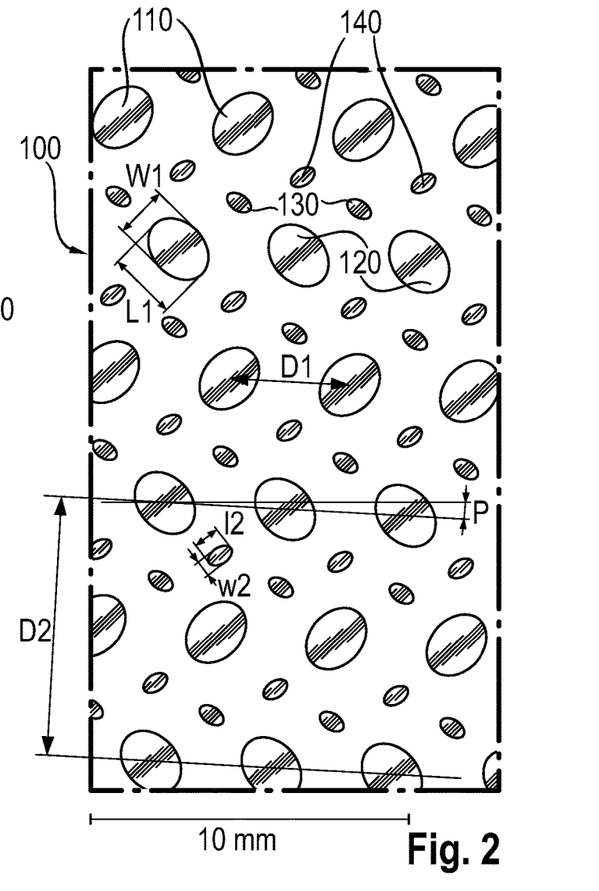
FIG. 2 shows a close-up of the bonding pattern of FIG. 1 at a scale 5:1.

FIG. 1 illustrates a bonding pattern 100 for a nonwoven having thermal bonds of different sizes and orientations. FIG. 1 is at a scale of 1:1, while FIG. 2 is a close-up view at a scale of 5:1. The nonwoven extends in a machine direction (MD) and a perpendicular cross-machine direction (CD). This bonding pattern is discussed below for the purpose of illustration. The general considerations indicated above may of course be applied to modify the exemplified designs. For example in the example of FIGS. 1-2, the individual area of the larger bonds 110, 120 is 3.2 mm$^2$ and the individual area of the smaller bonds 130, 140 is 0.36 mm$^2$, and there are twice as many smaller bonds than larger bonds, but the ranges indicated previously may be applied to modify any of these values. The larger bonds on one hand and the smaller bonds on the hand may have the all same individual areas as shown. Of course it is not excluded that the larger and/or the smaller bonds have different areas within the range indicated. It is also not excluded that other bonds are present that are neither large or small as defined in the claims. The bonding pattern 100 may comprise at least three, in particular four or more different type of bonds 110-140, wherein each type of bonds is defined by size, shape and orientation of its major direction.

The bonding pattern 100 illustrated in FIGS. 1-2 comprises larger bonds 110, 120 and smaller bonds 130, 140. All the bonds have a generally rounded (in particular elliptical) shape, with no sharp angles. As can be better seen on FIG. 2, the larger bonds comprise two types of larger bonds, wherein the first type 110 and the second type 120 of larger bonds are orientated in a different major directions while having the same size and shape. Similarly, the smaller bonds 130, 140 comprise a first type of smaller bonds 130 and a second type of smaller bond 140, having the same size and shape but oriented in different directions. In FIGS. 1-2, the bonds having the same size but having different orientations are symmetrically oriented relative to the machine direction, in particular they may be placed with their major direction being about perpendicular to each other (at an angle of about 90°). More generally, when the larger bonds comprise differently oriented larger bonds 110, 120, the angle formed by the major dimensions of the differently oriented larger bonds may be for example at least 20°, or at least 45° and thus up to 90°. Similarly, when the smaller bonds comprise differently oriented smaller bonds, these may be symmetrically oriented relative to the machine direction. The angle formed by the major dimensions of the differently oriented smaller bonds may be for example at least 20°, or at least 45° and thus up to 90°.

The larger bonds 110, 120 have a major dimension L1 measured along a major direction and a minor dimension W1 measured along a minor direction perpendicular to the major direction, and the smaller elongated thermal bonds 130, 140 have a major dimension l2 measured along a major direction and a minor dimension w2 measured along a minor direction perpendicular to the major direction.

The thermal bonds represented in the FIGS. 1-2 comprise a sub-pattern of six repeating rows, each row generally orientated parallel to the cross-machine direction, taking into account an optional but preferred pitch angle P. Each row may comprise a single type of thermal bonds having the same size, shape and orientation. As indicated previously, the pitch angle P measures the angle between the rows and the cross-machine direction (CD), and may typically range from 0 to 10 degrees relative to the cross-machine direction (CD). Having a non-zero pitch angle improves the properties of the bonding pattern by ensuring two consecutive rows of the same type of bonds are slightly shifted in CD direction. This can further improve the anti-fuzz properties of the bonding pattern. Although not illustrated, the pattern may also comprise rows generally oriented in MD having the pitch angle relative to MD. The repeat in width distance center-to-center D1 of two adjacent bonds in a given row may be, as illustrated, the same distance for all adjacent bonds. The repeat in height distance D2 between two rows of bonds of the same type is also the same for all the rows in the illustrated Figures. It is not excluded that other bonding pattern may have different repeat value in CD or MD although having the constant values for all the bonds of the same type may be simpler.

The following table summarizes the main dimension of the example of FIGS. 1-2, further indicating broader ranges in which the values may be modified as indicated in the general disclosure section above.

TABLE 1

Exemplary values for the dimension for the pattern of FIGS. 1-2

| Dimension | Value in FIGS. 1-2 | Indicative range |
|---|---|---|
| Ratio of the number of smaller bonds/larger bonds | 2:1 | 1 to 3 |
| Larger bond's area 110, 120 | 3.2 mm$^2$ | 1.0 mm$^2$-10 mm$^2$ |
| Smaller bond's area 130, 140 | 0.36 mm$^2$ | 0.10 mm$^2$ to <1.0 mm$^2$ |
| Larger bond's length L1 | 2.25 mm | at least 1.50 mm |
| Smaller bond's length l2 | 0.88 mm | less than 1.50 mm |
| Ratio L1/l2 | 2.56 | L1/l2 ≥ 1.5 |
| Larger bond's width W1 | 1.8 mm | 0.9 mm-3.6 mm |
| Smaller bond's width w2 | 0.52 mm | 0.26 mm-1.0 mm |
| Repeat in width D1 | 4.1 mm | 2 mm-8 mm |
| Repeat in height D2 | 8.6 mm | 4.0 mm-16 mm |
| Pitch angle p = | 3° | 0-10° |
| Total number of bonds/cm$^2$ | 17 | 5-58 |
| Bonded area | 22.1% | 17%-30% |

The pattern of thermal bonds shown can obtained by passing a nonwoven web through two calendaring rolls, at least one of the calendaring rolls having bonding protrusions. The protrusions are illustrated by FIGS. 3 and 4 showing cross-sections of the larger and smaller protrusions in their minor directions at a scale of 10:1. FIG. 3 illustrates a protrusion for providing the larger thermal bonds 110, 120, while FIG. 4 illustrates a protrusion for providing the smaller thermal bonds 130, 140. The protrusions have a height h1, h2 (also referred to as engraving depth), with typically h1 being equal to h2, and the side walls of the protrusions extend from the surface of the roll at angles $\alpha 1$, $\alpha 2$, with typically $\alpha 1$ being equal to $\alpha 2$. In the specific example shown, h1=h2=0.68 mm, $\alpha 1=\alpha 2=22°$.

In a first application example, polypropylene pigmented trilobal fibers comprising 0.3% TiO2 (by weight of the web) were formed into a web of fibers at a basis weight of 12 gsm using the spunbond process. The web was then immediately passed between calender rolls with one roll having the bonding pattern as shown in FIGS. 1-2. In a second example, the polypropylene pigmented trilobal fibers comprised 1% TiO2 by weight and the spunbond web had a basis weight of 17 gsm. The second web was also passed through calender rolls with the same bonding pattern. Both resulting nonwovens were used as a topsheet in a baby diaper. A printed signal present on the acquisition layer was clearly visible through the topsheet. Liquid management performance were good (rewet and liquid absorption). The TiO2 particles were introduced as an matting agent to reduce the shine of the nonwoven. The opacity of the first nonwoven was measured at 31% and of the second nonwoven at 45%.

FURTHER EXAMPLES

FIGS. 5 to 10 show further examples of bonding patterns 500-1000, that were computer generated. These bonding patterns also comprise larger bonds having all the same size and shape but oriented in two different directions, and likewise for the smaller bonds. The squares shown for FIGS. 5-10 have a side dimension of 40 mm. The exemplary dimensions of the bonds in these patterns are as indicated below in Table 2 below:

TABLE 2

Exemplary values for the dimension for the pattern of FIGS. 5-10

| Dimensions | Pattern 500 | Pattern 600 | Pattern 700-1000 |
|---|---|---|---|
| Ratio of the number of smaller bonds/ larger bonds | 2:1 | 2:1 | 2:1 |
| Larger bond's area | 2.8 mm$^2$ | 2.9 mm$^2$ | 3.2 mm$^2$ |
| Smaller bond's area | 0.56 mm$^2$ | 0.48 mm$^2$ | 0.37 mm$^2$ |
| Larger bond's length | 2.6 mm | 2.7 mm | 3.2 mm |
| Smaller bond's length | 1.1 mm | 1.1 mm | 0.9 mm |
| Larger bond's width | 1.4 mm | 1.4 mm | 1.3 mm |
| Smaller bond's width | 0.65 mm | 0.57 mm | 0.52 mm |
| Total number of bonds/cm$^2$ | 17 | 17 | 17 |
| Bonded area | 22.1% | 22.1% | 22.1% |

Test Method: Opacity

Opacity by contrast ratio measurements are made using a 0°/45° spectrophotometer suitable for making standard Hunter L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2 C ° and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors excise the topsheet specimen from the article for testing. Place the specimen flat against the instrument with the body facing surface toward the spectrophotometer's measurement port and the region of interest within the port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicates specimens.

Opacity is calculated by dividing the Y value measured using the black tile as backing, divided by the Y value measured using the white tile as backing, then multiplying the ratio by 100. Record opacity to the nearest 0.01%. Calculate opacity for the 10 replicates and report the average opacity to the nearest 0.01%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven extending in a machine direction and a perpendicular cross-machine direction, the nonwoven comprising fibers bonded by thermal bonds, wherein the thermal bonds comprise:
   larger elliptical shape bonds having an individual area of at least 1.5 mm$^2$; and
   smaller elliptical shape bonds having an individual area in the range of 0.10 mm$^2$ to 1.0 mm$^2$;
   wherein at least some of the larger elliptical shape bonds and the smaller elliptical shape bonds are disposed in rows generally aligned with the cross-machine direction;
   wherein the rows have a pitch angle ranging from 0 to 10 degrees relative to the cross-machine direction;
   wherein the smaller elliptical shape bonds are disposed between the rows of larger elliptical shape bonds; and wherein the ratio of the number of smaller elliptical shape bonds to the number of larger elliptical shape bonds is at least 1.5.

2. The nonwoven according to claim 1, wherein:
the larger elliptical shape bonds have a major dimension measured along a major direction, and a minor dimension measured along a minor direction perpendicular to the major direction;
the smaller elliptical shape bonds have a major dimension measured along a major direction, and a minor dimension measured along a minor direction perpendicular to the major direction; and
wherein the major dimension of the larger elliptical shape bonds is at least 50% higher than the major dimension of the smaller elliptical shape bonds.

3. The nonwoven according to claim 2, wherein the major dimension of the larger elliptical shape bonds is at least 2.0 mm, and wherein the major dimension of the smaller elliptical shape bonds is less than 1.0 mm.

4. The nonwoven according to claim 2, wherein at least some of the larger elliptical shape bonds have a ratio of the major dimension to the minor dimension ranging from about 1.05 to about 2.0, and wherein at least some of the smaller elliptical shape bonds have a ratio of the major dimension to the minor dimension ranging from about 1.10 to about 2.5.

5. The nonwoven according to claim 2, wherein at least some of the larger elliptical shape bonds and/or the smaller elliptical shape bonds have their major direction oriented at an angle of at least 10° relative to the machine direction of the nonwoven.

6. The nonwoven according to claim 2, wherein the larger elliptical shape bonds comprise differently oriented larger elliptical shape bonds, and wherein an angle formed by the major directions of the differently oriented larger elliptical shaped bonds is at least 20°.

7. The nonwoven according to claim 2, wherein the smaller elliptical shape bonds comprise differently oriented smaller elliptical shape bonds, and wherein an angle formed by the major directions of the differently oriented smaller elliptical shape bonds is at least 20°.

8. The nonwoven according to the claim 1, wherein the bonding area of all the thermal bonds represents from about 17% to about 30% of the area of the nonwoven.

9. The nonwoven according to claim 1, wherein a distance between two rows of the larger elliptical shape bonds is from about 2.0 mm to about 8 mm.

10. The nonwoven according to claim 1, wherein a distance center-to-center for at least some of the larger elliptical shape bonds in the same row ranges from about 2 mm to about 8 mm.

11. The nonwoven according to claim 1, having a basis weight ranging from 10 gsm to 20 gsm.

12. The nonwoven according to claim 1, wherein the nonwoven has an opacity index of from about 15% to about 50%.

13. An absorbent article comprising:
a topsheet on a wearer-facing side of the absorbent article;
a backsheet on a garment-facing side of the absorbent article; and
an absorbent core positioned at least partially between the topsheet and the backsheet;
wherein the topsheet and/or the backsheet comprises the nonwoven of claim 1.

14. A nonwoven extending in a machine direction and a perpendicular cross-machine direction, the nonwoven comprising fibers bonded by thermal bonds, wherein the thermal bonds comprise:
larger elliptical shape bonds having an individual area of at least 1.0 mm$^2$; and
smaller elliptical shape bonds having an individual area of less than 1.0 mm$^2$;
wherein at least some of the larger elliptical shape bonds and the smaller elliptical shape bonds are disposed in rows generally aligned with the cross-machine direction;
wherein the rows have a pitch angle ranging from 0 to 10 degrees relative to the cross-machine direction;
wherein the smaller elliptical shape bonds are disposed between the rows of larger elliptical shape bonds; and
wherein the ratio of the number of smaller elliptical shape bonds to the number of larger elliptical shape bonds is at least 1.2;
wherein the bonding area of all the thermal bonds represents from about 17% to about 30% of the area of the nonwoven.

15. The nonwoven according to claim 14, wherein:
the larger elliptical shape bonds have a major dimension measured along a major direction, and a minor dimension measured along a minor direction perpendicular to the major direction;
the smaller elliptical shape bonds have a major dimension measured along a major direction, and a minor dimension measured along a minor direction perpendicular to the major direction; and
wherein the major dimension of the larger bonds is at least 50% higher than the major dimension of the smaller bonds.

16. A nonwoven extending in a machine direction and a perpendicular cross-machine direction, the nonwoven comprising fibers bonded by thermal bonds, wherein the thermal bonds comprise:
larger elliptical shape bonds having an individual area of at least 1.0 mm$^2$; and
smaller elliptical shape bonds having an individual area of less than 1.0 mm$^2$;
wherein at least some of the larger elliptical shape bonds and the smaller elliptical shape bonds are disposed in rows generally aligned with the cross-machine direction;
wherein the rows have a pitch angle ranging from 0 to 10 degrees relative to the cross-machine direction;
wherein the smaller elliptical shape bonds are disposed between the rows of larger elliptical shape bonds; and
wherein the ratio of the number of smaller elliptical shape bonds to the number of larger elliptical shape bonds is at least 1.5;
wherein the larger elliptical shape bonds have a major dimension measured along a major direction, and a minor dimension measured along a minor direction perpendicular to the major direction;
wherein the smaller elliptical shape bonds have a major dimension measured along a major direction, and a minor dimension measured along a minor direction perpendicular to the major direction; and
wherein the major dimension of the larger elliptical shape bonds is at least 50% higher than the major dimension of the smaller elliptical shape bonds.

17. The nonwoven according to claim 16, wherein the major dimension of the larger elliptical shape bonds is at least 1.50 mm, and the major dimension of the smaller bond is less than 1.50 mm.

18. The nonwoven according to claim 16, wherein at least some of the larger elliptical shape bonds have a ratio of the major dimension to the minor dimension ranging from about 1.05 to about 2.0, and wherein at least some of the smaller elliptical shape thermal bonds have a ratio of the major dimension to the minor dimension ranging from about 1.10 to about 2.5.

* * * * *